(12) United States Patent
Shriver (10) Patent No.: US 8,709,059 B1
(45) Date of Patent: Apr. 29, 2014

(54) SUTURING AN EXPANDING, CONTRACTING GRAFT TUBE IN ARTERY SEGMENT PREVIOUSLY OCCLUDED

(71) Applicant: Edgar L. Shriver, Aventura, FL (US)

(72) Inventor: Edgar L. Shriver, Aventura, FL (US)

( * ) Notice: Subject to any disclaimer, the term of this patent is extended or adjusted under 35 U.S.C. 154(b) by 0 days.

(21) Appl. No.: 13/694,529

(22) Filed: Dec. 10, 2012

(51) Int. Cl.
*A61F 2/06* (2013.01)

(52) U.S. Cl.
USPC ............................ 623/1.1; 623/1.13; 623/1.22

(58) Field of Classification Search
CPC .................................. A61F 2/958; A61F 2/95
USPC ............. 623/1.1, 1.11, 1.12, 1.13, 1.18, 1.19, 623/1.2, 1.21, 1.22, 1.23, 1.36; 606/139, 606/148, 151, 153, 191, 192, 194, 195, 606/198; 128/898; 600/114, 434, 585; 604/164.01, 164.12, 164.13, 170.02
See application file for complete search history.

(56) References Cited

U.S. PATENT DOCUMENTS

| | | | |
|---|---|---|---|
| 3,334,629 A | 8/1967 | Cohn | |
| 3,494,806 A | 2/1970 | Brumlik | |
| 4,503,569 A | 3/1985 | Dotter | |
| 4,733,665 A | 3/1988 | Palmaz | |
| 4,893,623 A | 1/1990 | Rosenbluth | |
| 5,002,563 A | 3/1991 | Pyka | |
| 5,163,955 A | 11/1992 | Love et al. | |
| 5,197,978 A | 3/1993 | Hess | |
| 5,662,700 A * | 9/1997 | Lazarus | 606/194 |
| 5,810,870 A | 9/1998 | Myers | |
| 6,264,684 B1 | 7/2001 | Banas | |
| 6,652,570 B2 | 11/2003 | Smith | |
| 7,713,215 B2 | 5/2010 | Shriver | |
| 7,771,422 B2 | 8/2010 | Shriver | |
| 8,211,160 B2 * | 7/2012 | Garrison et al. | 623/1.13 |
| 8,409,224 B2 * | 4/2013 | Shriver | 606/144 |
| 2005/0131516 A1 * | 6/2005 | Greenhalgh | 623/1.13 |

OTHER PUBLICATIONS

U.S. Appl. No. 12/924,746, filed Apr. 10, 2010, Sariver

* cited by examiner

*Primary Examiner* — Dianne Dornbusch
*Assistant Examiner* — Robert Lynch (57) ABSTRACT

A spiral wire with shape memory wound to a small circumference for percutaneous introduction into an artery lumen has holding balloons gripping each end to control unwinding that increases and decreases circumference of a concentric graft tube against artery wall without under-sizing that creates dangerous gaps or over-sizing that promotes occlusion re-growth. Inflating holding balloons pushes ends of a plurality of tunnel arcs located at 2 mm intervals in rim around balloon circumferences tightly against graft tube whereupon push-rods within tunnel arcs simultaneously push out sharp circular sutures of memory material that return to original circular shape as they pierce and join graft tube and artery wall.

14 Claims, 3 Drawing Sheets

SUTURING AN EXPANDING, CONTRACTING GRAFT TUBE IN ARTERY SEGMENT PREVIOUSLY OCCLUDED

CROSS-REFERENCE TO RELATED APPLICATIONS

This is a new invention by the Inventor of prior art device U.S. Pat. No. 7,713,215, which discloses a means of percutaneously placing stiff sutures in seals which are in the shape of the end-to-side junction at each end of a second tube to openings made in a first tube on either side of an occlusion, and in application Ser. No. 12/924,746, after an occlusion is percutaneously removed or pushed aside from an artery lumen by another device, a graft tube is placed concentrically in the segment and its ends percutaneously sutured to healthy tissue on either side of the previously occluded segment. The device disclosed here has advantages over these, as well as other prior art inventions, and incorporation of some parts of prior patents may be required.

FEDERALLY SPONSORED RESEARCH

Not Applicable

SEQUENCE LISTING OR PROGRAM

Not Applicable

BACKGROUND OF THE INVENTION

1. Field of the Invention

The field generally relates to conduits for containing blood flow that replace original or previously replaced conduits, introduced into the body percutaneously and attached, either as free-standing around an occlusion in a artery lumen or as a lining concentrically located in the segment of artery lumen from which an occlusion has been removed or pushed aside by another device. The conduits have commonly used names such as graft tubes, artificial grafts, stent grafts, veins, or tissue engineered vessels (TEV) made from cells of patient's own body.

2. Objects and Advantages

The invention revealed here provides the following unique advantages over and avoids identified disadvantages of prior art:
1. there is no prior art for the alternative configuration of present invention that provides percutaneous placement of a biodegradable spiral support wire, graft tube and circular sutures as a scaffold for a vein or TEV to become free standing after sutured connections have healed into anastomoses and scaffold has biodegraded;
2. the prior art for percutaneously placing a plurality of sutures simultaneously to connect free standing or concentric conduits in the body is that of the present inventor and present invention has the advantages of removing a certain device part that the prior art device allows to remain in the body and adjusting graft tube to match size of artery lumen by increasing and decreasing size of a spiral support wire in the body;
3. some prior art stent grafts provide a graft tube with internal frame of metal which is permanently increased in size by inflating a balloon in its lumen, an identified disadvantage in that once increased in circumference it cannot be decreased and since under-inflating a stent graft creates gaps between graft and artery wall that can create life-threatening blood clots, stent grafts are typically overinflated by about 20% to avoid clots and this over-inflation contributes to the occlusion growing back—generally around the stent graft ends thus making it no more effective than if it were not used, whereas the invention revealed here has the advantage that the spiral wire support can be increased and decreased in diameter while in artery segment by winding or unwinding spiral to match graft tube and artery circumference throughout segment length thus avoiding disadvantages of both over- and under-sizing;
4. other prior art stent graft ends have spikes or hooks that pierce artery wall to hold stent grafts in artery segment, but ends so attached can be moved by pulsing blood and by re-growth of occlusion whereas present device has the advantage of placing circular sutures that securely fasten graft tube ends and artery wall so they cannot move in any direction;
5. present device places all sutures simultaneously within one minute whereas a skilled surgeon can place about one suture a minute thus time required to accomplish all suture placement is about 8-12% of time required for manual placement of from 12 to 8 sutures;
6. an alternative configuration of the present invention provides a means of slitting diseased artery segment to release graft tube from diseased segment and away from occlusion re-growth. This potential advantage cannot be achieved with spikes or hooks as they do not securely attach ends as do circular sutures;

SUMMARY OF THE INVENTION

The present invention provides a spiral wire as concentric support for a graft tube, both being made about the size of the pre-selected artery segment from which an occlusion has been removed or pushed aside by another device. The spiral is tightly wound to a smaller circumference for introduction into the lumen of the artery segment previously occluded and is unwound as distal and proximal holding balloons grip each end of spiral wire to control the increase and decrease in its circumference and length by increasing space between winds, thus pushing graft tube against artery wall without under-sizing which would create dangerous gaps and without over-sizing which would promote re-growth of occlusion and also, in an alternative configuration tapering to accommodate differences in artery circumference throughout a long segment such as from above to below knee. After spiral is expanded and contracted so graft tube matches the circumference of artery lumen, balloons at each end of graft tube are fully or over-inflated to push cuffs on ends of graft tube tightly against artery wall and circumference of each balloon is a holder rim slightly overhanging ball which has arc openings in overhang which are spaced about 2 mm apart and contain ends of tunnel arcs, tubes that contain circular sutures made of material with shape memory and having a sharp end against graft tube and blunt end against push-rods used for pushing circular sutures out of tunnel arcs. Circular sutures were made circular and forced into shape of tunnel arcs during manufacture and return to their original circular shape as they are released from the circular tunnel and as they pierce graft tube and artery wall which are each about 1 mm thick thus holding them together with sutures of 2 mm diameter about 2 mm apart. Circular sutures are pushed simultaneously in less than one minute, thus reducing the time required to place sutures manually which is one per minute for a skilled surgeon. The circular sutures may have barbs and may be made of metal or biocompatible polymers or biodegradable material. The graft tube and spiral support wire may also be made of biodegradable material such as polybutyl succinate (PBS) or polyanhydrides to serve as a scaffold for a vein or TEV in alternative configurations which biodegrade after anastomoses have formed at sutured points. A means is also provided for slitting the artery wall segment that was previously occluded to allow the graft tube to move outside that segment that contains atheroma known to grow around ends of a stent graft.

PRIOR ART

Prior Art References

| Prior Art References: | | |
|---|---|---|
| U.S. Pat. No., | Year, | Name |
| 3,334,629 | 1967 Aug. 08 | Cohn |
| 3,494,006 | 1970 Feb. 10 | Brumlik |
| 4,503,569 | 1985 Mar. 12 | Dotter |
| 4,733,665 | 1988 Mar. 29 | Palmaz |
| 4,893,623 | 1990 Jan. 16 | Rosenbluth |
| 5,002,563 | 1991 Mar. 26 | Pyka |
| 5,197,978 | 1992 Mar. 30 | Hess |
| 5,163,955 | 1992 Nov. 17 | McNamara |
| 5,662,700 | 1997 Aug. 02 | Lazarus |
| 5,810,870 | 1998 Sep. 22 | Myers |
| 6,652,570 | 2003 Nov. 25 | Smith |
| 6,264,684 | 2001 Apr. 24 | Banas |
| 7,713,215 | 2010 May 11 | Shriver |
| 7,771,422 | 2010 Aug. 10 | Shriver |
| 12/924,746 | 2010 Apr. 10 | Shriver |

Atherosclerosis is a disease that afflicts about 20 million people in the United States; more than any other life threatening disease. The Greek words "athero" means "gruel" and "sclerosis" "hardening," so the disease is also known as "hardening of the arteries." Today this gruel or atheroma is often called "plaque," a deposit of cells, calcium, debris, and cholesterol in artery walls or in walls of conduits used as arteries. The occlusion narrows the artery lumen and the outermost or adventitial layer of the artery, which has about 80% of the strength of the wall, and expands to compensate, but the net effect is that the lumen narrows. The plaque may rupture, cause blood clots, and/or calcify. The most extreme case is a chronic total occlusion (CTO of more than 99% occlusion for 3 months). An occlusion that narrows the artery to the point where it is incapable of delivering oxygen-carrying blood to muscles and organs beyond the occlusion requires intervention, surgical or percutaneous. There may or may not be symptoms or results from stress tests or EKG to indicate the need for intervention and a CTO is an indication for immediate surgical intervention. The arteries may be those of the heart or peripheral to the heart (usually legs). When the brain or heart is oxygen-deprived, death or impairment occurs rapidly. When muscles of the lower body are oxygen-deprived, death is slower but half those affected die within 10 years. There may or may not be pain symptoms in the legs and gangrene may be the first clear indication with amputation or surgical intervention required to avoid death. Atherosclerosis may be treated by diet and drugs but patients often do not follow diets and the effects of tobacco smoke are irreversible even if the person stops smoking. So intervention is necessary in about 2 million cases in the US each year. About 75% of interventions are by percutaneous means rather than by surgical means as risk and debilitation are less.

The gold standard treatment is a bypass graft placed by open surgery with its ends "grafted" to slits in the artery on each side of the occlusion thus carrying blood around it. The reason this is the gold standard is that a bypass graft remains functional about 7½ years on average until 50% of cases fail. This is much longer than the duration of percutaneous means but despite this advantage, bypass grafts require surgery that is risky and debilitating. A coronary artery bypass graft (CABG) starts with a sternotomy which splits the sternum and pulls apart the rib cage and usually continues with a heart/lung machine for oxygenating and circulating blood through the body for about an hour while the heart is intentionally stopped. After a CABG procedure a patient is in intensive care for a day or more, in hospital for a week and has a long recovery at home. This is done to allow the surgeon's hands to get to the non-beating heart to place about 8 sutures on each end of each bypass graft (sometimes more than 3 grafts,—as in a triple bypass procedure) and the rate at which a skilled surgeon can do this is about a minute per suture. A heart lung machine can be safely used for about an hour and a triple bypass would require 48 sutures or more. There are so-called "da Vinci" machines that can assist the surgeon's fingers to remain steady enough to place coronary bypasses through openings in the chest while the heart beats, but this machine is expensive and applicable to a limited number of cases. Open surgery to place a bypass graft in the lower body is not as debilitating but is risky and involves a long recovery time in comparison to percutaneous entry through a skin puncture, which allows most patients to go home the next day with almost immediate recovery. The most common catheter-based method of intervention is to enter the body through a skin puncture in the groin where the femoral artery is close to the skin. After percutaneous entry with a hollow needle piercing both skin and artery, a guidewire is advanced through the needle and through the vasculature and then it enters the narrow occlusion rather than going around it. A balloon on a catheter is then advanced over the guidewire and into the occlusion where it is inflated to push aside the occlusion and thus open the artery. But the occlusion starts to close (re-stenose) when the balloon is removed. Balloons used alone result in the occlusion remaining open about 2½ years on average until 50% of cases close again, i.e., fail. To keep the occlusion propped open, stents were developed in the 1990s. Stents are wire mesh tubes that increase the length of time balloon treatments last in coronary artery applications to about 5 years until 50% fail. But in the longer arteries and occlusions of the legs, stents are likely to fracture so tend not to be used thus balloons are used alone.

The bypass graft for coronary arteries, which are generally less than 5 mm diameter, must be a vein, usually harvested from the patient's leg. It lasts about 7A years on average until 50% of the bypass grafts need replacement. An artery of the leg is generally larger than 5 mm so the bypass graft around an occlusion in a leg artery can be made of artificial material. Resistance to flow in an artificial artery of less than 4 mm is too much for them to be of practical use. But resistance is minimized in some types of artificial graft tubes so that they will last almost 7½ years on average, i.e. until 50% of patients have experienced failed grafts. Therefore artificial bypass grafts are preferred in legs, but surgery is required to place them. Percutaneous treatments have largely replaced surgical bypass graft treatments but have not achieved the long duration of the bypass graft placed surgically. Therefore there are inventions for increasing the duration of percutaneous treatments including those for placing a bypass graft percutaneously in hope that it will last about 7½ years rather than 2½ years for balloon angioplasty alone or 5 years when a stent can be used. The problem of the occlusion growing back through the open mesh in stents was partially dealt with in 2005 by placing a substance on the stent that eluted over time to resist that growth. But that drug has created other problems, like blood clots that sometimes get caught in an artery of the brain causing a stroke. The fact that stents tend to fracture in the legs has given rise to alternatives called stent grafts and to complete removal of the occlusion rather than pushing it aside. Contrary to expectations, complete removal, by any of several methods, including scraping with a blade, laser, freezing, and a roto-rooter device, results in re-growth of the occlusion in a shorter time than by pushing it aside with a balloon. However, after such plaque removal, a stent graft may be placed with the intention of keeping the occlusion from growing back. Stent grafts are generally successful in preventing occlusions from growing back through the graft tube but the occlusions tends to grow back around the ends generally requiring repeat treatment in 50% of cases in less than 2½ years, and thus providing no improvement over a balloon alone without using the stent graft. These stent grafts have included ePTFE and heparin bioactive surfaces to inhibit intimal hyperplasia and re-growth of the occlusion. But the re-growth around the ends makes the duration for stent grafts no longer or even shorter than the duration for balloons alone. Each year in the US there are about 310,000 coronary artery bypass grafts (CABG) and 178,000 bypass grafts in legs placed surgically while there are more than 1.7 million percutaneous interventions. Balloon treatments have largely replaced surgical bypass graft treatments but they have not achieved the long duration of the bypass graft placed surgically.

It may be recognized that a successful combination of the effectiveness of bypass graft duration and the safety of percutaneous delivery would replace currently used means that have only one, not both. Prior art by the present inventor and by other inventors have described devices for combining means of placing a bypass graft around occlusions in coronary arteries outside the artery wall as done in CABG surgery with percutaneous entry. None of these devices has been proven by clinical trials that resulted in approval by the Food and Drug Agency (FDA) for use—not because the bypass graft failed to provide the longer duration, but mostly because the graft used was not of sufficient size or there were real or assumed problems with one or more steps in the percutaneous process of placing the graft. For instance, doubts have often been expressed about whether these prior art devices can accomplish re-entry into the artery after creating a passageway outside the artery wall. There is no such doubt about another means of re-entry after bypassing the occlusion between layers of the artery wall rather going outside the artery wall. That process, subintimal angioplasty, was originally developed in 1988 for treating CTOs in which the occlusion has no opening that can be entered with a balloon. It was originally accomplished with a collection of commonly available general purpose devices. The procedure was not extensively used, possibly because it requires substantial skill to use the collection of devices and it is counterintuitive to intentionally dissect two layers of an artery wall. But specialized devices are now available to make the process easier and to increase the number of cases that can be successfully treated. Prior art percutaneous devices are able to exit the artery lumen at the point of an occlusion, force a guidewire loop between intimal and medial layers of artery wall and re-enter the artery lumen after creating a passageway or false lumen between those layers that pass around the occlusion. Entering the true lumen from the false lumen is accomplished in about 80% of cases where it is attempted with one two devices that have been approved by the FDA and are in use today. Another simpler device is in clinical trials. The prior art devices are not further discussed in this background statement except for: 1. such device has been used to create the pre-selected situation described for use of the device revealed herein, specifically, the pre-selected segment of artery from which an occlusion has been wrapped in the intimal layer and pushed to the side by tamping balloons and 2. that such a device is the subject of a separate patent application by the present inventor for use with the bypass graft tube that is the subject of the invention revealed here. Further, the invention revealed here can be used with any one of several other devices that use means such as freezing, lasering, scraping, burr drilling, etc., to create the pre-selected situation of an artery segment from which the occlusion has been removed. There are hypotheses about why the re-growth occurs around stent graft ends that include the shape of the ends, and that ends move slightly with the pulse thus rubbing and irritating the artery wall to induce intimal hyperplasia that induces re-growth of the occlusion. There is a tendency for stent grafts to be overinflated about 20% which causes occlusion re-growth. Once overinflated, graft stents cannot be reduced in size. The tendency to overinflate is because leaving a gap between stent graft and artery wall will produce thrombus which is a risk of immediate failure and mortality. Research has shown that the shape of stent graft ends and long length of stent grafts in legs is not the problem. But over-sizing the graft tube to more than the natural diameter of the artery reduces duration markedly. Also, though a means of placing sutures percutaneously has been invented by present inventor, this means is not in use today to effect a secure closure such as that accomplished with sutures placed surgically. When placed surgically, a bypass graft goes around the occlusion so the problem of occlusion re-growth around the graft tube ends does not occur, but this may be because the graft tube is outside the artery and thus not in contact with the occlusion atheroma inside the artery. Another means of keeping atheroma away from the graft tube would be to slit the artery wall through the diseased section thus releasing graft tube from contact, but this means is not known to have been tried previously. Therefore this may or may not carry other consequences that are disadvantageous or dangerous.

The stent graft includes metal so is not biodegradable and thus not useful in combination with veins or tissue-engineered vessels (TEV) that are graft tubes made from the patient's own body cells. The TEVs duplicate the structure of the natural artery wall's three layers, and vascular endothelial growth factors may be used with these TEVs. But as long as surgery is needed to place them in the body, their use will be limited to a fraction of the relatively small number of cases still treated by surgery. An alternative configuration of the present invention provides a biodegradable scaffold and sutures to support veins and TEVs while they grow and heal into a true anastomosis connection with the artery.

The graft tube revealed here can have its size adjusted up and down to match the size of the natural artery, thus a distinct advantage over prior art. Also the means of expanding the graft tube is accomplished with a less forceful means than a stent in a stent graft, namely by a supportive spiral wire whose size is controlled by winding spiral more or less tightly. Also improving the connection of graft tube and artery wall at the graft ends with sutures rather than prior art spikes or hooks might prevent the occlusion from growing back around the ends. The present invention places sutures from inside the graft about 2 mm apart around the artery circumference which is the ideal configuration that a skilled surgeon tries to obtain by placing about one suture per minute. The circumference of coronary arteries is generally less than 15 mm which requires 6 to 8 sutures. Leg arteries are about 15 to 27 mm in circumference thus requiring from 8 to 13 sutures about 2 mm apart. The present invention also provides a means of slitting the previously occluded segment of artery with a blade in a balloon allowing the internal graft tube to move outside the artery and away from the atheroma of the occlusion and thus become almost as free standing as the bypass graft placed surgically which is known to have a 7½ year duration on average. The ends of graft tube must be securely anchored for this option to be exercised. Prior art of spikes and hooks does not provide this security. Avoiding recognized disadvantages in prior art is desirable, but whether this will result in longer patency can only be determined by experimentation and eventually clinical practice. It is also apparent that the alternative configuration of using biodegradable material in the present device will enable it to be used a scaffold for veins and TEVs for which there is no percutaneous prior art but only the surgical option. If duration of graft tube can be as long as 5 years, it might attract the million people in the US who are currently unidentified to be identified in a screening test with a simple blood pressure measurement taken at ankle and arm simultaneously and done at a local pharmacy.

A prior art patent for attaching a graft tube to a lumen wall from inside the lumen is the Lazarus U.S. Pat. No. 5,662,700 which describes an artificial graft and implantation method for a prosthesis graft placed inside a blood vessel and attached on each end by one or more "staples" to prevent migration. The "staples" are not bent during placement but are actually shown and described as sharp metal hooks. The objective of the hooks is the same as that of the circular sutures placed by the present invention, namely to connect the ends of a graft tube to the lumen wall in which it is concentrically located. Hooks may prevent the graft tube from moving in the direction the hooks are present but not in the direction their sharp ends are pointed. That space is open, not closed while circular sutures secure the graft tube from movement in all directions. The present invention describes circular sutures that may be metal wire or polymer that is biodegradable or biocompatible. Lazarus cites prior devices that used hooks as the means of attaching one surface to another. Since Lazarus does not mention any means for removing or pushing aside occlusions in order for the device to be put in place, his device may be intended for placing a graft inside an aneurysm rather than in an artery from which an occlusion has been removed and will re-grow.

Cohn, in U.S. Pat. No. 3,334,629 describes a means of attaching a device inside a blood vessel in which extensible vanes having sharp teeth on the ends engage the interior walls of a blood vessel for the object of keeping it fixed in place. This has similarities to the Lazarus device but not to the circular sutures of the present patent application.

Brumilik, in U.S. Pat. No. 3,494,006 describes a fastening device intended as an improvement over a "velcro" type fastener in that only one surface is provided with fastener means, the other being permanently attached to elongated bodies having at least one barb on the free end which is intended to penetrate and lodge in the article to which adhesion is desired. This is not the means proposed with the present device, namely using circular sutures for the connection.

Other cited prior art utilize some variation of an expandable stent inside a graft tube to attach to artery wall. These are generally called stent grafts and their disadvantages with respect to the device revealed here have been described in detail.

Prior U.S. Pat. No. 7,771,442 issued to the present inventor is for percutaneously using push-rods to push stiff sutures through artery wall and bypass graft in seals to connect ends of bypass graft that goes outside the artery around the segment containing the occlusion to openings made on either side of occluded segment as is done in open surgery. In patent application Ser. No. 12/924,746 from the present inventor, the ends of a graft tube placed concentrically in the section of artery lumen from which an occlusion has been removed are secured by circular sutures pushed in place by push-rods. This is also done in the present patent application, however the present patent application removes a certain small part from the body that is left in the body by prior patent application Ser. No. 12/924,746 and present application provides a means of increasing and decreasing circumference of graft tube to match size of artery segment that prior art does not provide. In U.S. Pat. No. 7,771,442 a combination seal and suture is described where stiff sutures are located in hollow sutures in the longitudinal stem portion of a seal attached to the end of a bypass graft and push-rods on the circumference of a balloon are used to push the sutures out of the longitudinal section of the seal through junction of bypass graft and opening in artery wall and into the seal flange located in artery lumen thus providing a fluid-tight connection that can become an anastomosis when a vein is used as bypass graft. The stiff sutures move in the direction they are pointed by the hollow sutures in which they are located. There is no tunnel in the flange for the stiff suture to enter, though there may be a trench to hold the stiff suture while it punctures a tunnel. Since the heart is in a sac of pericardial fluid there is no requirement for a device to pierce tissue except that of vessel walls.

That invention when used in arteries peripheral to the heart require piercing tissue in which vessels are located therefore another invention by Shriver, U.S. Pat. No. 7,713,215, describes a device for piercing and dilating tissue to make an opening in the side of the artery for the seal flange to enter the lumen of the artery and dilate a tunnel outside the artery in which to place the graft. The flange is pushed through this opening in the side of the artery to expand inside the artery lumen and thus fit against the lumen wall to receive the stiff sutures pushed from the stem section of the seal after they pass through the tissue on the edge of the opening in the side of the peripheral artery.

The present invention utilizes a circular cuff rather than a seal and the cuff is entirely inside the artery rather than half in/half out of the artery as are the stem and flange portions of the seal in U.S. Pat. No. 7,713,215. The present invention does not require an opening in the side of the artery because the graft tube, with circular cuffs on each end, is concentrically within the artery lumen. Circular sutures, manufactured with shape memory material in a circular configuration with one sharp and one blunt end are forced into a tunnel having a different shape. In the device revealed in application Ser. No. 12/924,746 this tunnel is in a tunnel housing that remains in the body as they contain the circular suture. In the present application the tunnel is part of the device that is removed from the body leaving only the circular suture. The circular sutures are pushed out of the tunnel with push-rods and shape memory causes the circular suture to curve as it pierces cuff and lumen wall as it returns to the circular shape. The circular sutures resist movement of graft tube and artery wall from each other in all directions whereas spikes or hooks used in other prior art in lieu of circular sutures allow movement in any direction that a spike or hook has not closed to movement. Circular sutures hold both ends of the graft tube in place in the artery lumen, thus providing a conduit of biodegradable or non-biodegradable material lining the diseased section of artery or vein. The occlusion is removed by one of the standard devices for that purpose before the graft tube is placed.

BRIEF DESCRIPTION OF THE DRAWINGS

FIG. 5C is a view of cuff which is the end of graft tube that is attached to artery wall by circular sutures.

FIG. 5D shows inflated holding balloon distal with holder rim and arc opening rim.

FIG. 5E shows artery and cuff of graft tube with a plurality of equally spaced sutures joining graft tube cuff and artery wall after all device components have been removed.

FIG. 6F is a side view of swivel receiver.

| Key | |
|---|---|
| 1. | Intimal layer |
| 2. | Medial layer |
| 3. | Adventitial layer |
| 4. | Tunnel arc |
| 5. | Graft tube |
| 6. | Spiral support wire |
| 7. | Occlusion |
| 8. | Delivery Catheter |
| 9. | Distal holding balloon |
| 10. | Artery |
| 11. | Advancing guidewire |
| 12. | Cuff |
| 13. | Distal holding catheter |
| 14. | Proximal holding catheter |
| 15. | Proximal holding balloon |
| 16. | Stylet wire |
| 17. | Holder rim |
| 18. | Artery wall |
| 19. | Circular suture |
| 20. | Push-rod |
| 21. | Push-rod base |
| 22. | Grip opening |
| 23. | Distal push-rod tube |
| 24. | Slitting catheter |
| 25. | Slitting balloon |
| 26. | Cuff spikes |
| 27. | Barbs |

-continued

| | Key | |
|---|---|---|
| 28. | Point truncated | |
| 29. | Point centered | |
| 30. | Spiral lumen | |
| 31. | Slitting blade | |
| 32. | Arc opening | |
| 33. | End grip opening | |
| 34. | Swivel receiver | |
| 35. | Tunnel arc swivel | |
| 36. | Push-rod tunnel | |
| 37. | Receiver opening | |
| 38. | Receiver | |
| 39. | Receiver open face | |
| 40. | Receiver closer ring | |
| 41. | Wire net | |
| 42. | Plunger | |
| 43. | Distal assist balloon | |
| 44. | Proximal assist balloon | |
| 45. | Proximal push-rod tube | |
| 46. | Medium wall segment | |
| 47. | Thin wall segment | |
| 48. | Thick wall segment | |

DETAILED DESCRIPTION OF THE INVENTION

Having thus described the figures, methods in accordance with the present invention are now described with reference thereto. It should be understood that steps described for each process may be omitted or the order changed or performed simultaneously without deviating from the spirit or scope of the invention. The following description should be read with reference to the drawings, in which the elements in different drawings are numbered in like fashion. The drawings, which are not necessarily to scale, depict selected embodiments and are not intended to limit the scope of the invention. Examples of construction, dimensions, materials, and manufacturing processes are provided for various elements but merely as a reflection of current manufacturing practices regarding processes and materials. Those skilled in the art will recognize that many of the examples provided have suitable alternatives in materials, manufacturing processes and specific configurations which may be utilized now and in the future to produce equivalent means.

Figures 1A, 1B:
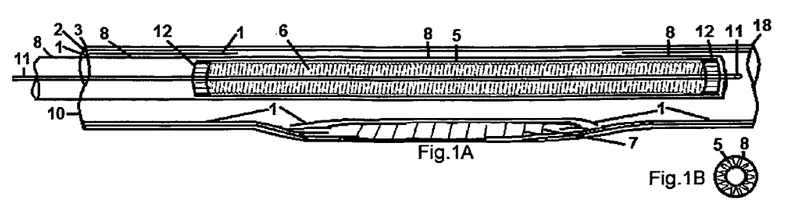
FIG. 1A shows an occlusion wrapped in an intimal layer pushed to one side of artery which is a pre-selected condition for use of device revealed here which is also shown.
FIG. 1B shows an example of an undulating wave shape folding pattern for graft tube.

FIG. 1A shows the situation that exists after the use of a subintimal angioplasty procedure that causes occlusion 7 to be wrapped in intimal layer 1 and pushed to one side of artery 10 by tamping balloons. This is the preferred pre-selected situation for use of the present device. It is not the only situation that may be pre-selected, the others being complete removal of the occlusion by any one of several other devices resulting in the artery lumen being essentially clear of any occlusion 7 and intimal layer 1 being in its normal location next to medial layer 2, angioplasty by balloon, and in an aneurysm. The pre-selected situation is referred to here with the short term of "segment of artery from which occlusion has been removed" and this term is intended to include the preferred situation where occlusion 7 is wrapped in layer 1 of artery wall 18 which has been tamped to the side of artery wall 18—as one means of removal. The particular situation represented in FIG. 1A is the preferred situation and it includes advancing guidewire 11, which is the J-tip guidewire with stylet wire 16 that was used in the previous subintimal angioplasty procedure and left in place for this procedure of placing graft tube 5. Guidewire 11 may be replaced with another guidewire that does not have a J-tip, and any guidewire used may have stylet wire 16 inside to help stiffen it. In FIG. 1A graft tube 5 is shown only in outline in order for the spiral support wire 6 to be seen as tightly wound. Spiral support wire 6 is seen as being tightly wrapped after being manufactured by one of optional manufacturing processes. For instance, a laser might be used to cut a spiral path around a tube or a wire of about 0.035 inch diameter, more or less, might be wrapped, with space between coils, on a mandrel, either process producing a spiral support wire 6 with circumference about equal to the circumference of the pre-selected segment of artery in which device is to be used. Spiral support wire 6 has a proximal and distal end with lumen spiral 30 therebetween and length between proximal and distal ends is selected to match the pre-selected length of segment of artery 10 that has had an occlusion removed from it. There is space between coils as in the spiral of a spiral bound notebook. This spacing is shown in other figures but not in FIG. 1A in which spiral support wire 6 is shown tightly wound to the smallest circumference possible which is when coils are touching as shown. As spiral support wire 6 is unwound it increases in length as well as diameter. Spiral support wire 6 is made of a material that has sufficient shape memory and resilience to easily return or be returned to its original manufactured circumference and shape by causing it to be unwound after being tightly wound to a smaller circumference. But the material must also not be so resilient as to force spiral support wire 6 to its original circumference if it meets resistance from the segment of artery wall 18 in which spiral support wire 6 is located. There are concentric tubes in which spiral support wire 6 is located, graft tube 5 and artery 10 in all configurations and delivery catheter 8 in one alternative configuration. Graft tube 5 is slightly flexible, sufficient to allow a shallow trough to form where spiral support wire 6 presses against it and graft tube 5 extends slightly outward to press against artery wall 18 on the adventitial side of graft tube 5 opposite such a trough on the inside. Delivery catheter 8 is made of flexible elastic material such as a combination butyl polyimide and helps control expansion of spiral support wire 6 so it does not kink or spring out of general linearity as it unwinds and expands elastic delivery catheter 8. After spiral support wire 6 unwinds to expand, delivery tube 8 is removed from body leaving graft tube 5 almost touching artery wall 18. Artery 10 may be of unequal circumference at certain points throughout the pre-selected segment which graft tube 5 is expanded and contracted by operator rotating distal holding catheters 13 and proximal holding catheter 14 to first cause circumference of graft tube 5 to be larger than artery 10 circumference and then reduce circumference to match circumference of artery wall 18 by rotating in opposite direction. This is intended to allow some coils of spiral support wire 6 to be of larger diameter than others to fill gaps between artery wall 18 and graft tube 5. In alternative configurations graft tube 5 and spiral support wire 6 may be of tapered shape throughout their length to match circumference of artery throughout its length, generally only when artery segment is long, such as extending from above to below the knee as over that distance femoral artery tapers to popliteal artery which is of smaller circumference and this distance may be more than 200 mm in some cases. The objective that there be no gaps between circumferences of graft tube 5 and artery 10 has been stated, thus spiral support wire 6 should expand to slightly greater circumference to eliminate such gaps but a countervailing objective is not do so with such force as to expand artery 10 to greater than its natural circumference and that objective is met by rotating distal holding catheters 13 and proximal holding catheter 14 to cause reduction and by making spiral support wire 6 of appropriate material, wire diameter and method of treatment during manufacture. One material likely to fit these characteristics is a polymer but some types of metal may also meet the requirement. For example a metal such as spring steel of a particular cross-section of wire might be more likely to meet the requirement than would a heat treated nickel titanium compound which produces a stronger urge to return to its original circumference, but with the proper cross-section either might meet the requirement after prototype studies are conducted. Spiral support wire 6 made of polymer material has the same requirements as noted for a metal wire but in addition there is a requirement for an alternative configuration that biodegrades and is absorbed by the body after being the scaffold on which a vein or TEV from patient's own body is used as graft tube 5 and anastomoses have formed to connect them to artery wall. The scaffold requires bio absorbable materials such as poly (butylene succinates) as spiral support wire 6 and also as circular sutures 19 as described with FIGS. 4A-C. The biodegradable material must also meet the requirements of shape memory and wire diameter to return to original shape after deformation with the appropriate degree of force as can be ascertained by experimentation, that is, wire diameters, materials and heat treatment such as cause the spiral support wire to exert sufficient force to fill gaps between graft tube 5 and artery wall 18 without exerting so much force that artery wall 18 is forced to a greater than normal circumference. When tightly wound, lumen spiral 31, of support wire 6, is about half the diameter of artery 10 which makes lumen spiral 30 of sufficient circumference to contain the device parts for placing circular sutures as shown in subsequent figures. Artery 10 ranges from about 4-5 mm diameter in coronary arteries to 5-10 mm in peripheral arteries so size is pre-selected for conditions in each case. On each end of graft tube 5 is cuff 12 of the same material and integral to graft tube 5. Cuff 12 is the only portion of graft tube 5 that is shown by other than outline in FIG. 1A. This device is for percutaneously unwinding and winding a spiral support wire inside a graft tube to increase and decrease size of said graft tube until equal to size of a pre-selected segment of artery and placing circular sutures through ends of said graft tube and said segment of artery to securely join them.

In FIG. 1B an example of how graft tube 5 may be folded to reduce its circumference to being slightly larger than that of tightly wound spiral support wire 6. This can be accomplished with many different folding patterns and the example here shows it folded in an undulating wave shape.

Figure 1C:
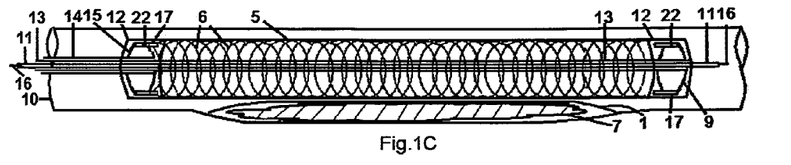
FIG. 1C shows a spiral support wire pushing against a graft tube inside a delivery catheter.

In FIG. 1C distal holding balloon 13 and proximal holding balloon 14 are shown holding cuffs 12 of graft tube 5 in place at a distance from distal holding catheter 13 and proximal holding catheter 14 that is almost enough to cause graft tube 5 to touch artery wall 18. Delivery catheter 8 has been removed at this point in the procedure or, as an alternative configuration, it has not been used. Distal holding balloon 9 and proximal holding balloon 14 are constructed of a combination of non-compliant and compliant materials. The non-compliant material maintains the balloon shape as shown and discussed in FIG. 3A until the device is received and made ready for use. In FIG. 1C the alternative configuration of delivery catheter 8 has been withdrawn (or was not used) as graft tube 5 approaches artery wall 18 and is almost touching at which point artery wall 18 assumes the function of preventing spiral support wire 6 from kinking and springing out of being generally straight. Spiral support wire 6 is shown as partially, but not yet fully expanded, so it is approaching but not yet pushing against artery wall 18. As spiral support wire 6 gets larger it causes artery wall to become somewhat straighter and it should be noted that space is increasing between coils of spiral support wire 6 as it expands. Since spiral support wire 6 is located within (unfolding) graft tube 5, it also unfolds and expands graft tube 5 while moving toward artery wall 18. The ends of spiral support wire 6 are located in grip opening 22 of holder rim 17 and held there by the pressure of their compression while (tightly wound) and after distal holding balloon 9 and proximal holding balloon 15 are partially inflated, the ends being held by pressure of inflation on holder rim 17 as shown in greater detail in FIGS. 2A-D. Spiral support wire 6 has a tendency to unwind to reach its original manufactured circumference so distal holding catheter 13 and proximal holding catheter 14 are turned to control spiral support wire 6 as it unwinds.

Figure 2A:
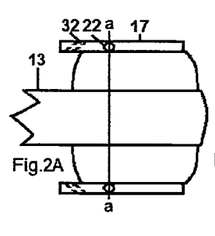
FIG. 2A shows a holder rim on circumference of holding balloon distal, both made of non-compliant material to maintain their shape as shown.

FIG. 2A shows holder rim 17 on the circumference of distal holding balloon 9. Proximal holding balloon 15 is also shown with holder rim 17 on its circumference but this is in reverse to distal holding balloon 9, so the description in the specification is termed to refer to distal holding balloon 9 though meant to refer equally to proximal holding balloon 15. Holder rim 17 is made of a stiff but somewhat flexible material attached to or part of the outer circumference of distal holding balloon 9. The non-compliant material typically used to make stiff balloons is an example of such material which is used in combination with compliant material to manufacture distal holding balloon 9 and proximal holding balloon 15.

The portion of distal holding balloon 9 shown in FIG. 2A is made of compliant material. The compliant material enables balloon inflation as shown and discussed with FIG. 2B. Holder rim 17 extends in the proximal direction a distance of about 4 mm, more or less, on the rim or circumference from distal holding balloon 9. The shape of holder rim 17 is like a steel rim on a wooden wheel that is wider than the wooden wheel so extends in an overhang toward the inside of the wheel. Holder rim 17 is about 1 mm thick and has arc opening 32, of less than 1 mm diameter, passing through its thickness at an angle in the overhang and to which it is attached (as shown). Holder rim 17 also has grip opening 22, of diameter about equal to diameter of spiral support wire 6, passing into its width from edge of holder rim 17 about 3 mm to end at end grip opening 33. Grip opening 22 and arc opening rim 32 are at approximately right angles to each other. Arc opening rim 32 is shown as being at an acute angle with respect to longitudinal axis of distal holding catheter 13. This angle changes as tunnel arc 4 changes its angle with inflation of distal holding balloon 9 thus causing arc opening rim 32 to twist to a less acute angle. This is discussed further in conjunction with FIGS. 3A and 4A. Grip opening 22 is further discussed with respect to FIG. 2A. The distal end of spiral support wire 6 is placed in and pushes against end grip opening 22 when distal holding balloon 9 and spiral support wire 6 is tightly wound during the manufacture and assembly process. The force of spiral support wire 6 to unwind keeps the end of spiral support wire 6 pushed against end grip opening 33 and thus in grip opening 22. The means of controlling the longitudinal axis of lumen spiral 30, from kinking and springing was discussed in connection with delivery catheter 8 and FIG. 1C.

Figure 2B:
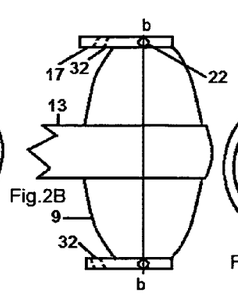
FIG. 2B shows a holding balloon inflated thus increasing in circumference and squeezing grip opening and arc opening in holder rim.

FIG. 2B shows distal holding balloon 9 inflated as enabled by the portion of distal holding balloon 9 that is made of compliant material. This inflation squeezes holder rim 17 and though made of non-compliant material, holder rim 17 compresses slightly causing grip opening 22 to squeeze the end of spiral support wire 6 located in grip opening 22.

Figure 2C:
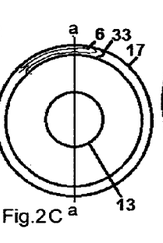
FIG. 2C is a cross-sectional view of non-compliant material of uninflated holding balloon and holder rim holding end of spiral support wire in grip opening as it presses against end grip opening.

FIG. 2C shows a cross-sectional view. The end of spiral support wire 6 occupies grip opening 22 for only a short distance of about 3 mm from end grip opening 33 to edge of holder rim 17. Thus the end of spiral support wire 6 is shown with a broken line indicating it is not in grip opening 22 beyond that distance which is a sufficient distance to hold end tightly.

Figure 2D:
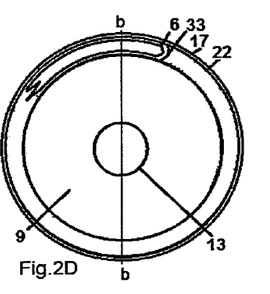
FIG. 2D is a cross-sectional view with holding balloon inflated so that end of spiral support wire is now firmly squeezed by compressive pressure of inflated holding balloon.

FIG. 2D shows distal holding balloon 9 inflated with end of spiral support wire 6 as shown in FIG. 2C, but the end is now gripped by compressive pressure of distal holding balloon 9 on holder rim 17 thus gripping end of spiral support wire 6 as distal holding catheter 13 and proximal holding catheter 14 rotate in opposite directions because spiral support wire 6 is being allowed to return to the circumference it was originally made in, with operator doing the final rotating of distal holding catheter 13 and proximal holding catheter 14 to adjust spiral support wire 6 and close any gap between graft tube 5 and artery wall 18 of artery 10 as seen on fluoroscopy or as felt by operator to bring spiral support wire 6 to the shape shown in FIG. 1C.

Figure 3A:
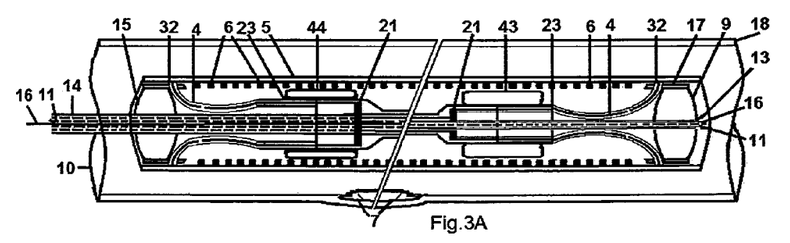
FIG. 3A shows the situation after distal and proximal holding balloons have been partially inflated which does not change shape from that maintained by non-compliant material but makes balloons more resistant to deformation.

FIG. 3A shows the situation as device is manufactured, assembled and delivered to physician for use. The non-compliant material of which distal holding balloon 9 and proximal holding balloon 15 are made keeps the shape shown but physician partially inflates distal holding balloon 9 and proximal holding balloon 15 before entering device into body through percutaneous entry. This does not change the shape but makes balloons more resistant to deformation that might occur during introduction in body. In this alternative configuration delivery catheter 8 is not used so is not shown but distal holding balloon 9 and proximal holding balloon 15 are considered to have been partially inflated. Thus ends of spiral support wire 6 are gripped in grip opening 22 though not as strongly held as when distal holding balloon 9 and proximal holding balloon 15 are fully inflated. Spiral support wire 6 is shown here as a series of round black spots to represent the cross-section view of each coil. It may be seen how the ends of a plurality of tunnel arcs 4 are located in arc opening rim 32. Since distal holding balloon 9 and proximal holding balloon 15 are only partially inflated the plurality of tunnel arcs 4 are generally in line with longitudinal axis of lumen spiral 30 of spiral support wire 6 they thus twist arc openings 32 of holder rim 17 at an acute angle. This twisted acute angle is possible because holder rim 17 has some flexibility even though it is made of stiff, so called, non-compliant material. Distal push-rod tube 23 and proximal push-rod tube 45 flare to their larger diameter from smaller diameter catheters that extend to operator located outside the body. The flare is shown as an angle from smaller to larger diameter. Each proximal push-rod tube 45 and each distal push-rod tube 23 has a thick wall segment and a thin wall segment to be described in greater detail with FIGS. 6A-F. The proximal portion is functionally the same as the distal portion but in reverse and a gap is shown between distal and proximal portions to indicate that there is a variable distance between distal and proximal portions depending on the case involved which could be substantially more than 200 mm or as short as 30 mm.

Figure 3B:
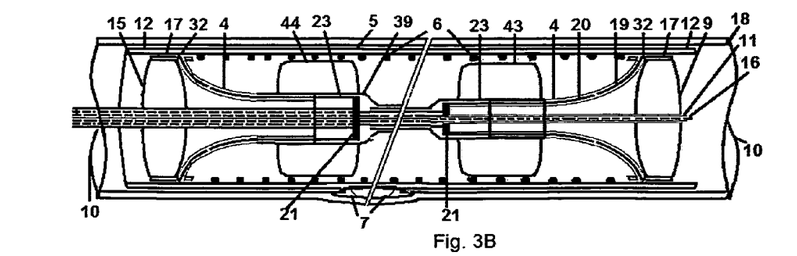
FIG. 3B shows the situation after distal and proximal holding balloons have been fully inflated to adjust spiral support wire 6 and graft tube to circumference of artery and place tunnel arcs against cuffs at a less acute angle than they previously had.

FIG. 3B shows the situation after distal holding balloons 9 and proximal holding balloon 15 have been fully inflated to adjust spiral support wire 6 and graft tube 5 to match circumference of artery 10. This movement of tunnel arcs 4 from their previous acute angle to a less acute angle causes twisting of arc opening rim 32 in holder rim 17. Thus holder rim 17 is made of a material that tolerates this amount of twisting while also being sufficiently stiff and resilient to hold proximal ends of tunnel arcs 4 in place to point toward cuffs 12 on each end of graft tube 5 and thus putting circular sutures 19 in position to pierce cuffs 12 and artery wall 18 to suture them together. The material known as "non-compliant" often used for certain types of medical balloons generally includes a weft and woof of fabric which is actually slightly flexible in the direction needed by this twisting action. Distal assist balloon 43 and proximal assist balloon 44 are mounted on, and their fluid lines provided in the walls of distal push-rod tube 23 and proximal push-rod tube 45. Since it is customary for fluid lines to be located in the walls of the catheter on which balloons are mounted, no fluid lines are shown in these figures. Distal assist balloon 43 and proximal assist balloon 44 are shown fully expanded and they assist distal holding balloon 9 and proximal holding balloon 15 by helping to allow the holding balloons to change the distance their altitude is from the end of push-rod tubes as they expand with tunnel arc 4 remaining a constant length.

Figure 4A:
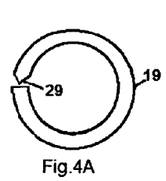
FIG. 4A shows circular suture made in the shape of a circle with a blunt end and a sharp end touching each other. The sharp end is in the shape of a pencil point, called point centered.

By viewing FIGS. 3A and 4A together it may be seen that distal holding balloon 9 moves in the proximal direction with inflation of distal holding balloon 9 because tunnel arc 4 remains as a constant length as the hypotenuse of a right triangle whose other two sides are 1. the increasing altitude distance of holder rim from distal holding catheter 13 as distal holding balloon 9 inflates, and 2. the distance of the base of altitude of holder rim 17 from distal push-rod tube 23 which must therefore decrease in the proximal direction. Generally speaking this is a 3, 5, 6 triangle which has 30, 60 and 90 degree angles. With the plurality of tunnel arcs 4, each is curved rather than straight so these are approximate. The plurality of distal tunnel arcs and proximal tunnel arcs has each tunnel arc being a tube of strong, smooth, slightly flexible material with distal end, proximal end and lumen therebetween and being in the shape of a curved arc of a large oval with length of said arc being longer than circumference of a circular suture plus a push-rod, inside diameter slidably larger than diameter of one of a plurality of circular sutures and one of a plurality of said push-rods which are both located inside said tunnel arc, and having an outside diameter slidably smaller than said arc opening rim in which each said distal end of said tunnel arc is connected and length being such as to extend from said arc opening rim to an attachment on distal end a distal push-rod tube or from said arc opening rim on said proximal holding balloon to proximal end of a proximal push-rod tube 45. Arc tunnel 4 is made of hard, smooth material so push-rod 20 and circular suture 19 will slide within the slidably larger inside diameter of tunnel arc 4 and a slippery substance may be added to facilitate this movement. The material may be slightly flexible in one alternative configuration in which tunnel arc 4 is bent to a smaller circumferential arc as distal holding balloon 9 is inflated to bring distal end of tunnel arc 4 to artery wall 18. This alternative configuration avoids the need for an articulation joint to connect tunnel arcs 4 to distal push-rod tube 23 and proximal push-rod tube 45 by tunnel arc swivel 35 and swivel receiver 34 as described in connection with FIGS. 6A-J. The physician decides if spiral support wire 6 and graft tube 5 are properly placed with respect to artery wall 18. If so, the suturing process is started, if not the distal and proximal holding balloons are deflated, device removed, and tamping balloons introduced to eliminate gaps, then device is again advanced, holding balloons inflated and suturing process started.

FIG. 4A shows one of a plurality of circular sutures 19, being a wire of metal or polymer made in the shape of a circle of about 2 mm diameter with a blunt end and a sharp end touching each other. Sharp end is shown in the shape of a pencil point and called point centered 29. In prior prototype studies, prototypes of circular sutures 19 and push-rods 20 were made from a heat treated nickel titanium compound and forced into tunnels of different shapes. Circular sutures 19 returned to their original circular shape as they were pushed out of confinement in that tunnel by push-rods 20. Though this material has been successfully used in such prototype experiments, other materials, such as stainless steel or spring steel appear to be viable options for circular sutures, as well as for push-rods and spiral support wire. Biocompatible polymers of various types and wire diameters are also appropriate materials to meet this requirement as are biodegradable, absorbable synthetic materials such as polymers made from poly(glycolic acid), poly(butylene succinates) or two components with different thermal characteristics, oligo(ϵ-caprolactone)diol and crystallisable oligo(ρ-dioxanone)diol, which are heat treated to return to original configuration after slight heating as provided by body temperature, as needed for alternative configuration scaffolds. These same materials may be tried in order to meet the somewhat different requirements of spiral support wire 6 as well.

Figure 4B:
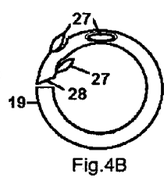
FIG. 4B shows circular suture with barbs on its surface. The point is shown as an alternative configuration called point truncated.

FIG. 4B shows circular suture 19 with barbs 27 on its surface. The barbs prevent circular suture 19 from backing up once pushed out of tunnel arc 4. The sharp end is shown as truncated as an alternative configuration called point truncated 28. A truncated point will tend to change its direction of travel through tissue in the direction opposite its flat face and this characteristic may be useful in urging circular suture to its original diameter.

Figure 4C:
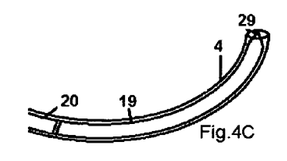
FIG. 4C shows circular suture forced into the shape of tunnel arc and push-rod placed to push circular suture out of tunnel arc.

FIG. 4C shows circular suture 19 forced into the shape of tunnel arc 4 and push-rod 20 placed to push circular suture 19 out of tunnel arc 4. A plurality of push-rods 20 are made the same diameter as said circular sutures 19 of material that is slightly flexible and resistant to deformation with shape straight or slightly curved like shape of said tunnel arc 4 in which push-rods 20 and circular sutures 19 are located with end of push-rod against blunt end of circular suture 19 and sharp end of circular suture at distal end of tunnel arc 4 and circular suture 19 returns to its original circular shape as it is pushed out of tunnel arc 4 by push-rod 20.

Figures 5A, 5B, 6A, 6B, 6C, 6D, 6E:
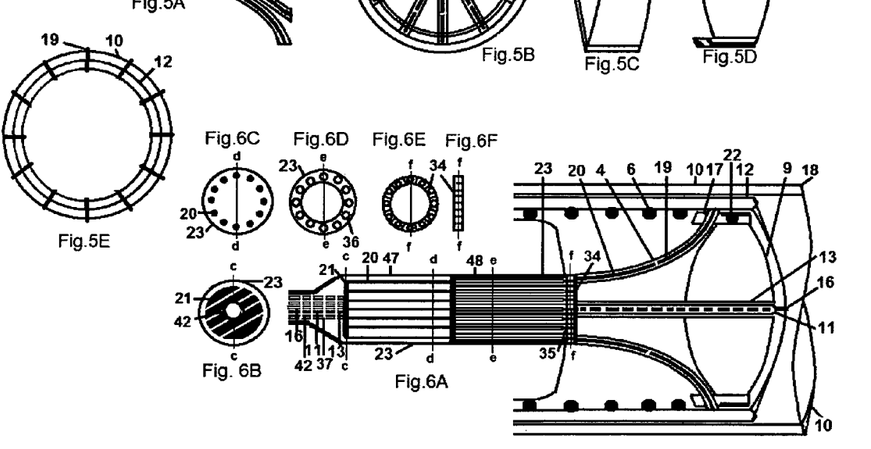
FIG. 5A shows a side view of seven tunnel arcs in the 12 o'clock to 6 o'clock positions to represent 12 o'clock positions used here to represent a plurality of tunnel arcs.
FIG. 5B is a longitudinal view of what is shown in side view in FIG. 5A plus holder rim, graft tube, cuff and artery.
FIG. 6A is a detailed side view of the situation at distal end before operator begins to push a plurality of push-rods in push-rod tube so all circular sutures are pushed simultaneously through cuff and artery wall.
FIG. 6B is a cross-sectional view of push-rod base, plunger and push-rod tube at cross section c.
FIG. 6C shows push-rods, inside push-rod tube at cross section d.
FIG. 6D shows push-rod tunnels in push-rod tube at cross section e.
FIG. 6E is a cross-sectional view of swivel receiver which is part of an alternative configuration.

FIG. 5A shows a side view of a plurality of tunnel arcs 4 containing a plurality of circular sutures 19 and plurality of push-rods 20. The plurality is generally shown as 12 throughout figures and descriptions but often all 12 cannot be seen in a given view. In FIG. 5A, seven tunnel arcs 4 are shown in the 12 o'clock to 6 o'clock positions continuing proximally from their distal ends through distal push-rod tube 23 to their proximal ends at push-rod base 21. Circular suture 19 is seen as a segment with distal end coincident with distal end of tunnel arc 4 and continuing proximally about 6 mm inside tunnel arc 4. Circular suture 19 is made about 6 mm long as the circumference of a circle of 2 mm diameter is about 6 mm. Circular suture 19 is intended to encircle artery wall 18 and graft tube 5 and each of these is about 1 mm thick, thus about 2 mm thick in total. Graft tube 5 may be made somewhat less than 1 mm and made of a material that is strong but somewhat elastic. Elastic properties enable a tube to expand and contract slightly with blood from a beating heart and to form shallow grooves where spiral support wires 6 presses against graft tube 5. The distal end of push-rod 20 is contiguous with proximal end of circular suture 19 and continues inside tunnel arc 4 through push-rod tunnels 37 in distal push-rod tube 23 to end and be attached to push-rod base 21 in distal push-rod tube 23. Plunger 36 is attached to push-rod base 21 which when pushed by operator pushes all push-rods 20 causing all circular sutures 19 to be pushed out of tunnel arcs 4. Not shown in FIG. 5A is the way tunnel arcs are lodged in arc grip openings 33 in holder rim 17.

FIG. 5B is a longitudinal view of what is shown in side view in FIG. 5A plus holder rim 17, graft tube 5, cuff 12 and artery 10.

FIG. 5C is a view of cuff 12 which is normally attached to or part of graft tube 5 and is shown here as the location where distal holding balloon 9 is inflated. At proximal end of spiral support wire 6 there is also cuff 12 on graft tube 5 where proximal holding balloon 15 is inflated.

FIG. 5D shows distal holding balloon 9 with holder rim 13 and arc opening rim 32. Arc tunnel 4 is held in arc opening rim 32 while holding balloon distal 9 is uninflated and inflated as shown here. As distal holding balloon 9 is inflated it moves holder rim 17 and arc opening rim 32 outward and since tunnel arc 4 is lodged in arc opening rim 32 it thus moves outward also thus twisting arc opening rim to different angles as distal holding balloon 9 is inflated and moves in the proximal direction.

FIG. 5E shows artery 10 surrounding cuff 12 of graft tube 5 with a plurality of sutures 19 (placed at 12 locations around circumference in this example) after all device components have been removed.

FIG. 6A provides a detailed side view of the initial situation before operator begins to push a plurality of push-rods 20 in push-rod tube 23 so all circular sutures 19 are pushed simultaneously through cuff 12 and artery wall 18. Of a plurality of circular sutures 19, two are shown inside tunnel arcs 4 at the 12 o'clock and 6 o'clock positions. Operator has inflated distal holding balloon 9 thus pressing holder rim 17, held in arc opening rim 32, against cuff 12 of graft tube 5. Circular suture 19 is shown in tunnel arc 4 where it was placed during assembly and thus forced into the shape of tunnel arc 4 rather than the circular shape in which it was made during manufacture. Being located at end of tunnel arc 4, immediately adjacent distally to push-rod 20, sharp end of circular suture 19 will be pushed out and through cuff 12 and artery wall 18 as circular suture reassumes its original circular shape as it leaves the confined shape of tunnel arc 4. Push-rod 20 continues proximally through distal push-rod tube 23 to be attached to push-rod base 21. Proximal push-rod tube distal and proximal push-rod tube 45 are larger diameter tubes that flare from smaller diameter tubular catheters as shown. The cross-sectional shape in distal push-rod tube 23 is shown in cross-sectional views. Distal push-rod tube 23 has a thin wall segment 47 where cross sections c and d are located and a thick wall segment 48 where cross-sections e and f are located. This also applies to proximal push-rod tube 45 which is of larger circumference and oriented in the opposite direction as distal push-rod tube 23, but only one end is shown.

FIG. 6B is a cross-sectional view of push-rod base 21, plunger 42 and distal push-rod tube 23 at cross section c. Each is attached to its own catheter that extends outside the body to the operator. The material of which they are made should be strong, and since plunger 36 is itself the catheter it must also be flexible while the others should be inflexible using a material such as a polymer which will bond with the catheter to which it is attached. The operator pushes plunger 42 which pushes push-rod base 21 forward in distal push-rod tube distal 23. In proximal push-rod tube 45, operator pulls plunger 42 rather than pushing it, as all actions are reversed with proximal push-rod tube 45 elements.

FIG. 6C shows push-rods 20, inside distal push-rod tube 23 at cross section d. Push-rods 20 do not touch wall of distal push-rod tube 23 in this thin wall segment 47 so are unsupported and thus may be prone to accidental bending. To prevent this, an alternative configuration with medium wall segment 46 is described with FIG. 8A.

FIG. 6D shows a view of cross section c of distal push-rod tube 23 which is in thick wall segment 48, manufactured to be sufficiently thick to contain push-rod tunnels 36 that are slidably larger than push-rods 20 so as to support push-rods 20 as they move through push-rod tunnels 36 as plunger 42 is pushed.

FIG. 6E shows a cross-sectional view of swivel receiver 34 at cross section e which is in thick wall segment 48. Swivel receiver 34 is part of an alternative configuration for articulating tunnel arc swivel 35 on the proximal end of tunnel arc 4. This is used only when tunnel arc 4 is made of a stiff material rather than a flexible material which bends to allow tunnel arc 4 to meet different shape requirements with distal holding balloon 9 inflated or partially inflated.

FIG. 6F is a side view of swivel receiver 34.

Figure 6G:
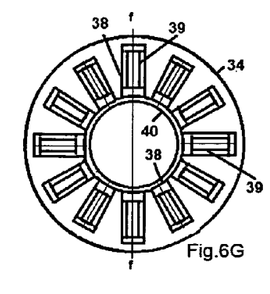
FIG. 6G is a longitudinal view of swivel receiver at cross-section f.

FIG. 6G is a longitudinal view of the alternative configuration of swivel receiver 34 at cross section f. Swivel receiver 34 is an alternative to that of a slightly more flexible tunnel arc 4 that simply bends rather than articulating. Tunnel arc swivels 35 located on the proximal ends of each tunnel arc 4, allow push-rods 20 to continue through swivel receiver 34 whether tunnel arcs 4 are at the uninflated angle shown in FIG. 3A or in the inflated position shown in FIG. 4A and these two angles of tunnel arc 4 are also represented in FIG. 6I and FIG. 6J.

Figures 6H, 6I, 6J, 6K:
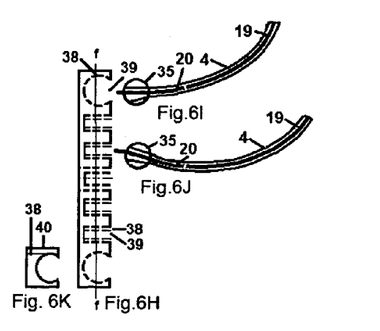
FIG. 6H is a side view of swivel receiver which receives the tunnel arc swivel.
FIG. 6I shows tunnel arc swivel on the end of tunnel arc in one position.
FIG. 6J shows tunnel arc swivel on the end of tunnel arc in another position.
FIG. 6K is a detail of a receiver closer ring used during assembly process to lock tunnel arc swivels in receiver openings.

FIG. 6H is a side view of swivel receiver 34 which receives the tunnel arc swivels 35 shown on the ends of tunnel arcs 4 in different positions in adjacent FIGS. 6I and 6J.

FIG. 6K is a detail of a receiver closer ring 40 which is also shown in FIG. 6G and is used during manufacture and assembly to lock tunnel arc swivels 35 in receiver openings 38 after they are placed through the central opening.

Figure 7A:
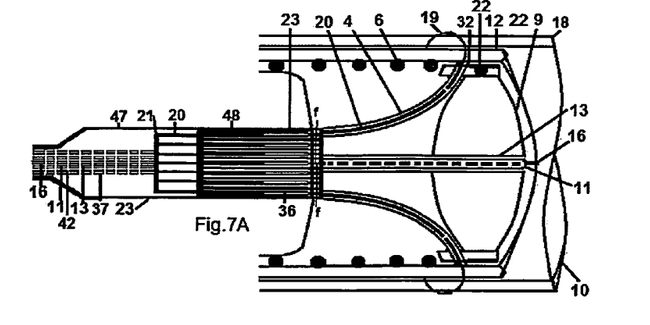
FIG. 7A shows the results of operator pushing plunger about half way through its travel.

FIG. 7A shows the results of operator pushing plunger 42 about half way through its travel. Push-rods 20 are pushed about half way through push-rod tunnels 36 and circular sutures 19 are pushed about half way around their circular path through graft tube 5 and artery wall 18.

Figure 7B:
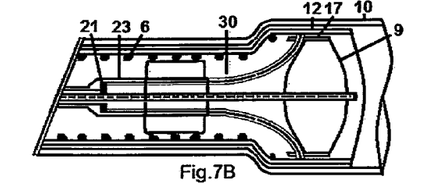
FIG. 7B shows the result of overinflating holding balloon distal which stretches artery wall the way a needle does going through the somewhat elastic artery wall.

FIG. 7B shows an option the operator may use; that of overinflating distal holding balloon 9. This causes no harm as spiral support wire 6 returns to the normal circumference of artery wall 18 after the over inflation. The purpose is to stretch artery wall 18 the way a needle going through the somewhat elastic artery wall 18 does when placing a suture manually. By pre-stretching artery wall 18 the circular suture may more easily pierce artery wall 18. It may also be noted that point truncated 28 may be used on circular suture 19 with flat side to tissue outside the circular pathway to thus cause circular suture 19 to follow this pathway rather that make a pathway larger than about 6 mm in circumference.

Figure 8A:
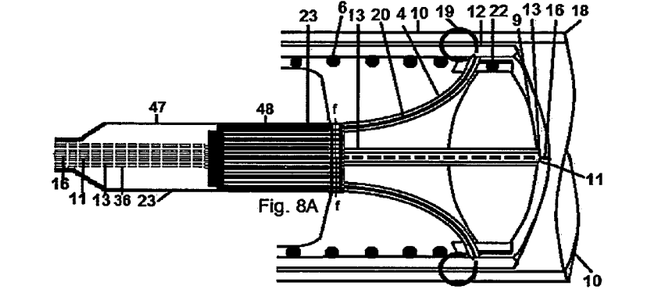
FIG. 8A shows plunger having pushed push-rod base against push-rod tube causing circular suture to complete its circular pathway to suture cuff of graft tube to artery wall.

FIG. 8A shows plunger 42 has pushed push-rod base 21 against distal push-rod tube 23 causing circular suture 19 to complete its circular pathway to suture cuff 12 of graft tube 5 to artery wall 18.

Figure 8B:
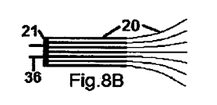
FIG. 8B shows an alternative configuration in which push-rod is not continued in the same diameter all the way to push-rod base.

FIG. 8B shows an alternative configuration in which push-rod 20 is not continued in the same diameter all the way to push-rod base 21. The object of this configuration is to make push-rod 20 more resistant to accidental bending in thin wall segment 47 of distal push-rod tube 23.

Figure 8C:
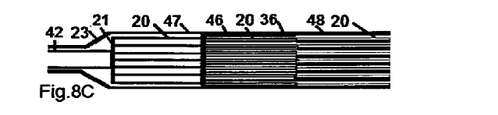
FIG. 8C shows changes in push-rod tube that are required with alternative configuration of push-rods of different diameters.

FIG. 8C shows changes in distal push-rod tube 23 that are required with alternative configuration of different diameters of each push-rod 20 shown in FIG. 8B. A medium wall segment 46 is provided between thin wall segment 47 and thick wall segment 48. The push-rod tunnel 36 in medium wall segment 47 is slidably larger than the larger diameter of a portion of push-rod 20 which allows passage of this larger diameter portion of push-rod 20 which is more resistant to accidental bending than is the smaller diameter portion of push-rod 20. The entry of the large diameter portion of push-rod 20 in push-rod tunnel 36 of medium thick wall segment 46 pushes the small diameter portion of push-rod 20 out of medium thick wall segment and if the smaller diameter of push-rod 20 bends it is only a short distance to support from wall. This alternative configuration may be used with flexible or articulated tunnel arcs 4 but swivel receiver 34 is not shown in this figure. The same alternative configuration applies to proximal push-rod tube 45 but with description stated in reverse.

Figure 9A:
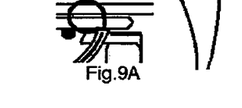
FIG. 9A shows circular suture with tunnel arc and holder rim inside cuff of graft tube before removal of device from artery.

FIG. 9A shows circular suture 19 with tunnel arc 4 and holder rim 17 inside cuff 12 of graft tube 5 before removal of device from artery 10.

Figure 9B:
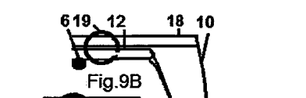
FIG. 9B shows circular suture after device has been removed from artery holding cuff of graft tube to artery wall.

FIG. 9B shows circular suture 19 after device has been removed from artery 10 holding cuff 12 of graft tube 5 to artery wall 18.

Figures 10A, 10B:
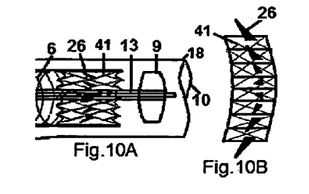
FIG. 10A shows an alternative configuration of cuff of graft tube in which wired cuff with cuff spikes is used in place of circular sutures.
FIG. 10B shows wired cuff expanded with cuff spikes changing angle at which they point as wire net changes angles with expansion.

FIG. 10A shows an alternative configuration of cuff 12 of graft tube 5 in which wired cuff 41 with cuff spikes 26 is used in place of circular sutures 19 to hold graft tube 5 to artery wall 18. Wired cuff 41 is increased in diameter by inflating distal holding balloon 9 in its lumen and cuff spikes 26 turn to point toward artery wall 18 as the net of wire to which cuff spikes 26 are attached change angles with expansion. Wired cuff 41 has the disadvantage of all stent types, that it cannot be reduced in circumference once it is increased. Wired cuff 41 may require such over inflation in order for cuff spikes 26 to pierce artery wall 18. It is possible that such over inflation in such a small section as represented by the wired cuffs 41 may not result in the same extensive irritation to artery 10 as does over inflation throughout the length of graft tube 5. This alternative configuration has the advantage of being much simpler to install than are circular sutures 19 but it lacks their secure fastening. The spiral support wire 6 provides the same advantages with this configuration as with the alternative configuration with circular sutures 19, so this configuration may be desirable for certain applications and is thus included for such possibilities.

FIG. 10B shows wired cuff 41 expanded with cuff spikes changing angle at which the point as wire net changes angles with expansion.

Figure 11A:
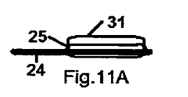
FIG. 11A shows an inflated slitting balloon on its slitting catheter with slitting blade extended.

FIG. 11A shows an inflated slitting balloon 25 on its slitting catheter 24 with slitting blade 31 extended. This device is similar to a single blade atherectomy device for removing plaque from an artery wall 18. However it is of such a size and shape as to slit artery wall 18 rather than remove plaque from it without injury to artery wall 18. Thus slitting blade 31 is about 1 mm in height, slitting catheter about 1 mm in diameter, and slitting balloon 25, made of non compliant and compliant material is about 1 mm when uninflated and when inflated with the inflation merely causing slitting blade 31 to extend 1 mm above outside thickness of inflated slitting balloon 25.

Figure 11B:
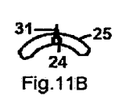
FIG. 11B shows a cross-sectional view of an inflated slitting balloon on its slitting catheter with slitting blade extended.

FIG. 11B shows a cross-sectional view of an inflated slitting balloon 25 on its slitting catheter 24 with slitting blade 31 extended. It is readily seen that slitting balloon 25 has a curved shape. This is because compliant material is used in the sides of slitting balloon 25 to allow this curved expansion but non compliant material is used to maintain the thickness of slitting balloon 25 when inflated and uninflated.

Figure 11C:
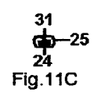
FIG. 11C shows an uninflated slitting balloon on its slitting catheter with slitting blade located in slitting balloon rather than as extended.

FIG. 11C shows an uninflated slitting balloon 25 on its slitting catheter 24 with slitting blade 31 in slitting balloon 25 rather than as extended. This device is for slitting the segment of artery 10 from which an occlusion has been removed and in which graft tube 5 has been placed. Slitting balloon 25 does not slit the segment of artery wall in which cuffs 12 are located as that is healthy tissue. Slitting balloon 25 is curved to fit on the adventitial side of graft tube 5. When slitting blade 31 is to be used that is predetermined and slitting catheter 24 placed adventitial to graft tube 5 while cuffs 12 on graft tube 5 are attached to artery wall 18 (it is not appropriate to use slitting balloon 25 with alternative configuration with cuff spikes 26 as they are not as secure as circular sutures 19. Slitting catheter 24 is withdrawn with slitting balloon 25 inflated and slitting blade 31 slitting artery wall 18 to proximal cuff 12 where slitting balloon 25 is uninflated and slitting catheter 24 removed between two adjacent circular sutures 19 which are about 2 mm apart. It is not known what the effects of slitting this segment of artery wall 18 will be. Experimentation with animals will be required to study this. It is merely recognized that it may be desirable to slit this segment as it releases graft tube 5 as a bypass graft placed surgically which is known to have a duration of about 7½ years and that the slitting separates the atheroma of the occlusion from graft tube 5, possibly making it difficult or impossible for the occlusion to grow back into graft tube 5.

What is claimed is:

1. A device for percutaneously winding and unwinding a spiral support wire inside a graft tube to increase and decrease size of said graft tube until equal to size of a pre-selected segment of artery and placing circular sutures through ends of said graft tube and said segment of artery to securely join them, comprising:
   a. said spiral support wire made of biocompatible material in the shape of a spiral binding with a spiral lumen as found on a spiral notebook with original length and diameter pre-selected to be about equal to that of said pre-selected segment of artery and able to be increased and decreased in length and diameter by winding and unwinding while in said segment of artery,
   b. said graft tube made of elastic biocompatible material in the shape of a tube with wall thickness less than 1 mm, length and circumference being about equal to that of said pre-selected segment of artery and containing said spiral support wire,
   c. a distal holding balloon mounted on a distal holding catheter and a proximal holding balloon mounted on a proximal holding catheter, with each of said distal and said proximal holding balloons made of a combination of compliant and non-compliant material,
   d. a holder rim being in the shape of a flat circular rim of compliant material mounted on a circumference of each said distal holding balloon and said proximal holding balloon and said holder rims being of a width greater than a width of said circumference of said holding balloons thus forming respective overhangs about said circumferences of said distal holding balloon in the proximal direction and said proximal holding balloon in the distal direction,
   e. a grip opening through a side edge of each of said holder rims being slidably larger than ends of said spiral support wire which are held in said grip openings by inflation pressure,
   f. a plurality of arc openings each made in the shape and size of one end of a plurality of tunnel arcs and each runs at an acute angle through said overhang in each said holder rim at equally spaced intervals of about 2 mm,
   g. a plurality of circular sutures of wire diameter about 0.2 mm, made of shape memory material in the shape of a circle of about 2 mm diameter and having one sharp end and one blunt end,
   h. a plurality of push-rods of same diameter wire as said plurality of circular sutures but being of a straight shape and made of material that is resistant to deformation, and being located contiguously with said plurality of circular sutures,
   l. a plurality of tunnel arcs, each being a tube of strong, smooth flexible material with a distal end, a proximal end and a length of lumen therebetween and each said tunnel arc being in the shape of an arc of a large oval with length of each said tunnel arc being at least twice as long as a circumference of one of said plurality of circular sutures, and having said lumen of diameter slidably larger than said wire diameter of one of said plurality of circular sutures and having an outside diameter slidably smaller than said arc opening in said holder rim in which each said distal end of each of said plurality of tunnel arcs is inserted and connected and each said tunnel arc extends either from each said arc opening on said rim of said distal holding balloon to attach to a distal push-rod tube or from said arc openings on said rim of said-proximal holding balloon to a proximal push-rod tube,
   j. said proximal push-rod tube and said distal push-rod tube are catheters that flare from a smaller diameter to a larger diameter and the smaller diameter section of said distal push-rod tube is slidably received within the smaller diameter section of said proximal push-rod tube and each said larger diameter section has a thin wall segment and a thick wall segment with lengths being approximately equal to said circumference of said circular sutures and said thick wall segment having wall thickness to slidably receive said tunnel arcs which are attached to said thick wall segment and each said thick wall segment having a plurality of push-rod tunnels within said wall thickness that are in line with and slidably larger than said push-rods that pass through said push-rod tunnels and said thin wall segment having wall thickness such that a push-rod base will pass through without touching said thin wall section except on a circumference of said push-rod base,
   k. two said push-rod bases each being a flat disc of inflexible material to which ends of said plurality of push-rods are attached on one side, and a plunger is attached on the other side and said two push-rod bases being made in two diameters one slidably smaller than inside diameter of said thin wall segment of said distal push-rod tube and the other of said thin wall segment of said proximal push-rod tube,
   l. two said plungers one attached to each said push-rod bases and being catheters, one sized to be slidably received within the other,
   whereby said device is configured to interact with body parts during use wherein, said spiral support wire located inside folded said graft tube is tightly wound and advanced on a pre-existing guidewire to a segment of artery previously cleared of an occlusion and is allowed to unwind there while operator controls unwinding by controlling rotation of concentric said proximal and said distal holding catheters to which said distal holding balloon and said proximal holding balloon are attached and on each said balloon circumference is said holder rim having said grip opening in which one end of said spiral support wire is held as said distal holding balloon and said proximal holding balloon are partially inflated and then fully inflated as said spiral support wire is unwound causing it to become the size of its original manufacture which was pre-selected to be the same length and circumference as said segment of artery which is to be treated, whereupon operator makes final adjustments to increase and decrease said spiral support wire circumference by twisting said proximal and said distal holder catheters and also simultaneously causing the full inflation of said distal and said proximal holding balloons which also brings said holder rim on said circumference of said holding balloons tightly against said graft tube and an artery wall where said sharp ends of said plurality of circular sutures located in said plurality of tunnel arcs equally spaced around said holder rim are also brought against said graft tube and said artery wall because each said tunnel arc is attached in one of said arc openings in said holder rims whereupon operator pushes said plunger located in said distal push-rod tube while holding said distal push-rod tube which pushes said distal push-rod base in the distal direction which pushes said push-rods in said push-rod tunnels located in said thick wall segment of said distal push-rod tube to which said tunnel arcs are attached and said push-rods push said circular sutures out of said tunnel arcs and into said graft tube and through said artery wall and as circular sutures are released from said tunnel arcs they return to their original circular shapes by the shape memory of the material of which they are made thus connecting said graft tube and said artery wall securely by said plurality of circular sutures, and the same procedure is then followed for said circular sutures in said proximal push-rod tube and said device is then removed from the body leaving said graft tube sutured on both ends to said artery wall throughout said segment of artery previously occluded.

2. The device of claim 1 further including:
a delivery catheter made of elastic material that readily expands from a circumference slidably larger than said folded graft tube to a circumference slidably smaller than said pre-selected artery segment,
whereby said delivery catheter with said folded graft tube and said spiral support wire inside is configured to be advanced to said pre-selected artery segment as its elasticity helps control expansion of said spiral support wire by inhibiting said spiral support wire from kinking and/or springing out of its spiral shape as it unwinds, then said delivery catheter is removed from body as it approaches said artery wall.

3. The device of claim 1 wherein;
said shape end of said circular suture is a centered point in the shape of a pencil point,
whereby said centered point is configured to be urged equally in all directions by passage through tissue.

4. The device of claim 1 wherein;
said shape end of said circular suture is a truncated point in the shape of a flat side created by truncation that also creates a sharp edge,
whereby said truncated point is configured to be urged in a direction opposite said flat side by passage of said sharp edge through tissue.

5. The device of claim 1 wherein;
a connection of each of said plurality of tunnel arcs to each of said proximal push-rod tube and said distal push-rod tube is by a, tunnel arc swivel and a swivel receiver consisting of,
a. a plurality of said tunnel arc swivels located on end of each of said tunnel arcs each being a cylinder of diameter slightly slidably smaller than thickness of said thick wall segment and thickness slidably greater than diameter of said tunnel arc, and which allow each said push-rod located in said tunnel arc to pass through said tunnel arc swivel when at any angle it is caused to assume,
b. said proximal and said distal push-rod tubes having ends sized to contain a plurality of swivel receivers, each swivel receiver being an opening in the end of each said push-rod tube sized to contain each of said plurality of tunnel arc swivels on an outside circumference but allowing each of said plurality of tunnel arc swivels to pass through on an inside circumference,
c. a plurality of receiver opening faces being openings in said inside circumferences of said plurality of swivel receivers that allows said plurality of tunnel arc swivels to extend through said opening faces during assembly,
d. two receiver closer rings of a size to close said opening faces on said inside circumference of said thick segment of said push-rod tube to hold each said tunnel arc swivel in each of said plurality of swivel receivers when each of said two receiver closer rings is swaged in place during manufacture and assembly of device,
whereby said tunnel arc swivels are held in said swivel receivers while allowing said tunnel arcs to assume different angles as said holding balloons are inflated without causing said push-rods to be crimped or said tunnel arcs to bend.

6. The device of claim 1 wherein;
said spiral support wire comprises a shape memory comprising a heat treated nickel titanium compound that returns to memory shape when heated by body temperature,
whereby said spiral support wire having shape memory has a stronger urge than a wire made of stainless steel to return to its original shape in said pre-selected segment of artery when heated by being in the body after its deformation to a smaller diameter for introduction into said pre-selected segment of artery.

7. The device of claim 1 wherein;
said spiral support wire is made of a biocompatible polymer,
whereby the urge of said biocompatible polymer to return to an original shape after deformation is generally less than the urge of metal wire.

8. The device of claim 1 wherein;
said spiral support wire is made of biodegradable absorbable bioplastic material,
whereby said bioplastic material is configured to dissolve in the body after a certain amount of time leaving said graft tube unsupported.

9. The device of claim 1 further including:
a. two cuff one on each end of said graft tube being made with a wire net of metal which does not contract once increased in circumference by being inflated by said distal holding balloon and said proximal holding balloon,
b. said wire net has cuff spikes which are spikes or hooks connected to said wire net in such a way as to change angle in which they point as cuff circumference is increased,
whereby inflation of said distal holding balloon and said proximal holding balloon is configured to cause said cuff spikes to point toward said graft tube and said artery wall as said wire net expands thus piercing said cuff and said artery wall to hold said cuffs against artery wall in a less secure connection than that provided by said circular sutures.

10. The device of claim 1 further including:
a cutting assembly for slitting said pre-selected segment of artery after said graft tube has been securely fastened to said artery wall by said circular sutures, comprising
a. a slitting catheter of less than 2 mm diameter,
b. a slitting balloon, when uninflated, is of approximately the same diameter as said slitting catheter and that contains a crease in which a slitting blade is encased when uninflated and, when inflated, a wall of said crease becomes part of a circumference of said slitting balloon and said slitting balloon, when inflated, is configured to expand in a curved shape around said graft tube and pushes against said artery wall,
c. said slitting blade which is of about 1 mm in altitude with a blunt side attached to a bottom of said crease and a sharp edge opposite said blunt side,
whereby said slitting catheter and said slitting balloon, when uninflated, are configured to be sufficiently small to be placed between said circular sutures at proximal end of said preselected segment of artery and said slitting blade is exposed for about 1 mm outside said circumference of said slitting balloon when inflated at said distal end of said preselected segment of artery which slits said artery wall when said slitting catheter is drawn proximally by operator to a point where said pre-selected segment of artery ends whereupon operator deflates said slitting balloon and pulls said slitting catheter, said slitting balloon and said slitting blade out between adjacent said circular sutures.

11. The device of claim 1 further including:

distal assist balloon attached to said circumference of said distal push-rod tube and proximal assist balloon attached to said circumference of said proximal push-rod tube with fluid lines located in walls of said distal push-rod tube and said proximal push-rod tube, whereby inflation of said distal assist balloon and said proximal assist balloon pushes said spiral support wire in place to aid expansion and relieve pressure on said distal holding balloon and said proximal holding balloon.

12. The device of claim 1 further including;

barbs on said circular sutures, whereby said barbs prevent said circular sutures from backing up once pushed forward.

13. The device of claim 1 wherein;

a. said push-rods being of larger diameter between said push rod base and said thin wall segment, b. a medium wall segment of same size of and located between said thin wall segment and said thick segment having a plurality of push-rod tunnels that are slidably larger than said push-rods of larger diameter, whereby the increased strength of said larger diameter wire will help prevent bending of smaller diameter wire in said thin wall segment.

14. The device of claim 1 wherein;

said plurality of tunnel arcs are made of a flexible material that bends where connected to said distal push-rod tube and said proximal push rod tube.

* * * * *